United States Patent [19]
Haendle et al.

[11] Patent Number: 5,448,613
[45] Date of Patent: Sep. 5, 1995

[54] X-RAY DIAGNOSTICS INSTALLATION

[75] Inventors: Joerg Haendle; Heinz Horbaschek, both of Erlangen, Germany

[73] Assignee: Siemens Aktiengesellschaft, Munich, Germany

[21] Appl. No.: 160,654

[22] Filed: Dec. 2, 1993

[30] Foreign Application Priority Data

Jan. 14, 1993 [DE] Germany .................. 43 00 829.1

[51] Int. Cl.⁶ .............................................. H05G 1/64
[52] U.S. Cl. ................................. 378/98.7; 378/98.8
[58] Field of Search .............................. 378/98.7, 98.8

[56] References Cited

U.S. PATENT DOCUMENTS

| | | |
|---|---|---|
| 4,517,594 | 5/1985 | Horbaschek . |
| 4,901,336 | 2/1990 | Nishiki . |
| 4,982,418 | 1/1991 | Kuehnel . |
| 5,012,504 | 4/1991 | McFaul et al. . |
| 5,164,583 | 11/1992 | Aichinger ............... 378/98.7 |

Primary Examiner—Craig E. Church
Attorney, Agent, or Firm—Hill, Steadman & Simpson

[57] ABSTRACT

An x-ray diagnostics installation has an x-ray image intensifier video chain which includes a semiconductor detector composed of pixels arranged in a matrix, serving as the video pick-up and a detector for identifying the average image brightness at the output luminescence screen of the x-ray image intensifier within a predetermined image region. A first read-out circuit is provided for pixels of a first group in the image, which is operated with a read-out clock at a first frequency, and a second read-out circuit is provided for pixels of a second group distributed over the area of the semiconductor detector, which is operated with a read-out clock at a second frequency. The second frequency is higher than the first frequency. The output signals of the pixels of the second group are supplied to an evaluation circuit, and the output signals of the first group of pixels are supplied to the video chain. Image production parameters, such as image brightness, can be controlled on the basis of the output signals of the second group of pixels.

10 Claims, 1 Drawing Sheet

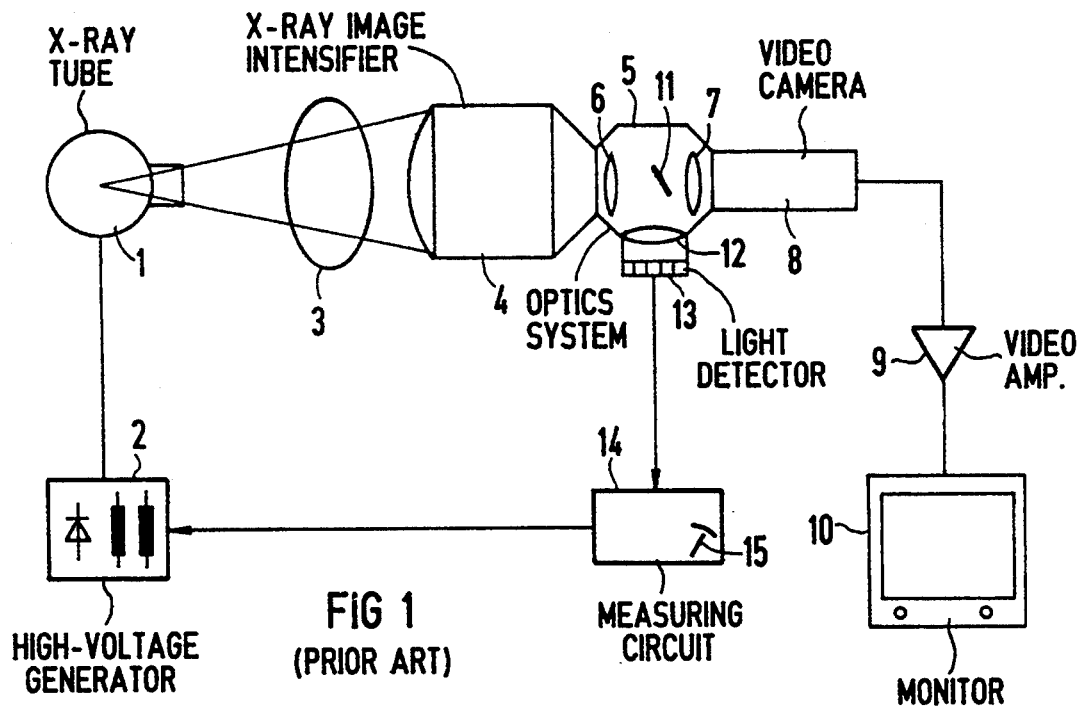
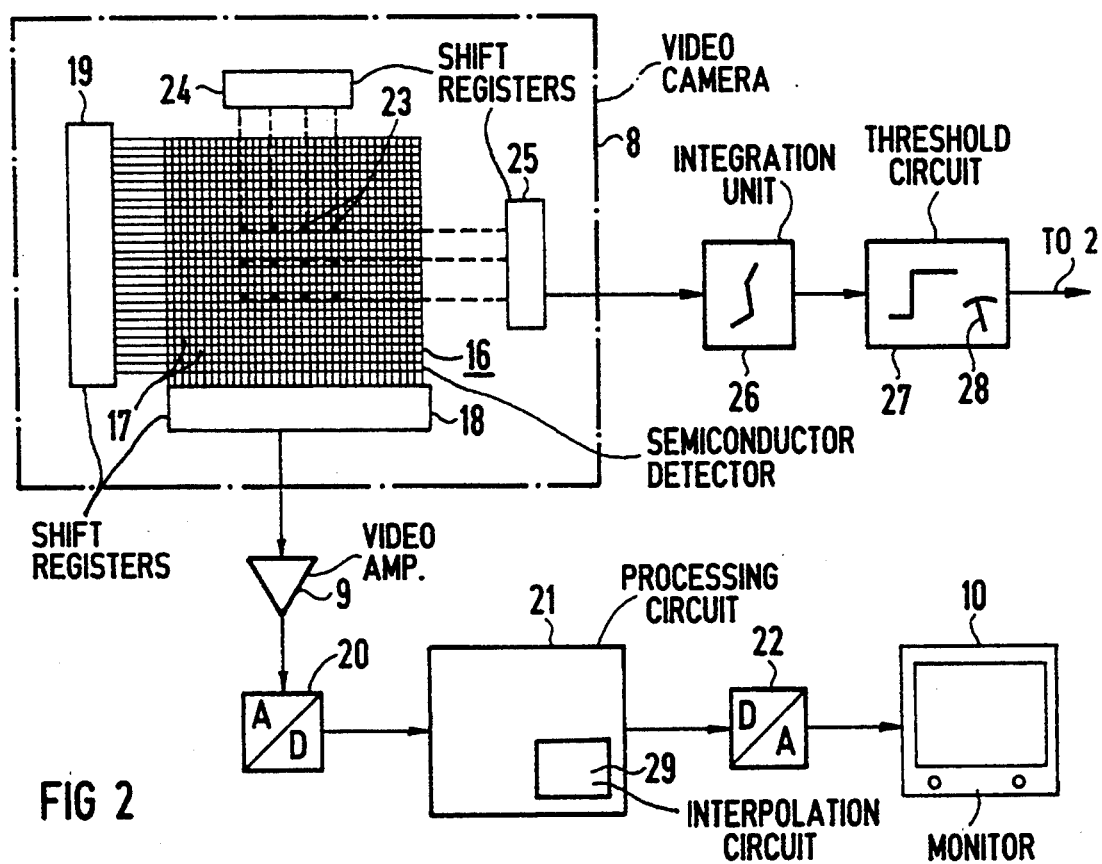

X-RAY DIAGNOSTICS INSTALLATION

BACKGROUND OF THE INVENTION

1. Field of the Invention

The present invention is directed to an x-ray diagnostics installation of the type having an x-ray image intensifier video chain with a video pick-up means coupled through an optic system to a detector for identifying the average image brightness within a predetermined region of the output luminescence screen of the x-ray image intensifier.

2. Description of the Prior Art

In x-ray diagnostics installation of the general type described above, the average image brightness, during an image exposure, is used to control the x-ray generator of the installation, so as to maintain the average brightness at, or within a range of, a specified value. Such an x-ray diagnostics installation is disclosed in U.S. Pat. No. 4,517,594 and European Application 0 362 427, wherein an image is coupled out in the parallel beam path of light distributor, the image being imaged by means of an optical system onto a detector array which is in the form of a matrix. The portion of the image used for controlling the exposure, known as the dominant, is selected with an adjustment means so that output signals of the detector elements selected in this manner are supplied to a comparator, wherein they are compared to a selectable (adjustable) specified value. The comparator controls the high voltage generator which supplies power to the x-ray tube of the x-ray diagnostics installation in accordance with the comparator output. A standard video camera having a video pick-up tube can be used as the video pick-up means, or alternatively a solid state image transducer, as disclosed in German OS 3842649, can be used. In known systems of this type, the necessity of having a light distributor (divider) and an additional detector for the dominant have proven to be disadvantageous.

An x-ray diagnostics installation is disclosed in U.S. Pat. No. 5,012,504 wherein the output signal of a video camera is supplied to the video chain for image processing, and to a control mechanism for the image brightness. A disadvantage of this know installation is that the control signal is only available synchronized with the video clock. A fast control and a chronologically arbitrary disconnect of, for example, the high voltage supply, is therefore not possible.

SUMMARY OF THE INVENTION

It is an object of the present invention to provide an x-ray diagnostics installation wherein a simple and exact selection of the dominant can be made with a low number of components.

The above object is inventively achieved in an x-ray diagnostics installation having a semiconductor detector serving as the video pick-up means, the semiconductor detector being composed of a plurality of pixels arranged in a matrix. A first read-out circuit is connected to the semiconductor detector which is operated with a read-out clock at a first frequency. A second read-out circuit is connected to the semiconductor detector with is operated with a read-out clock at a second frequency which is higher than the first frequency. The second read-out circuit drives a small number of image pixels, comprising a second group of pixels which are arranged in a specific distribution over the area of the semiconductor detector. The first read-out circuit effects a read-out of the remaining pixels of the image, constituting a first group of pixels. The output signals of the pixels of the second group are supplied to an evaluation circuit, the output of which is used to control imaging parameters, such as image brightness. The outputs of the pixels of the first group are supplied to the remainder of the video chain for processing to form a visually portrayable image.

Neither a light distributor nor a separate detector for the dominant is needed in the diagnostics installation of the invention since pixels of the semiconductor detector, which are illuminated in any event in the normal production of an image, are used to generate the control signal.

Preferably, the pixels of the second group are arranged along the sides of a rectangle, or on a circle, in a central region or area of the semiconductor detector. Since the output signals of the pixels in the second group are not available for use in the formation of the image, the "lacking" signals at the respective locations of the pixels of the second group can be inserted into the output signals of the first group of pixels by means of an interpolation circuit connected to the first group of pixels. The interpolation circuit interpolates the output signal or signals or one or more pixels in close proximity, such as adjacent, to each pixel of the second group. A reliable and fast disconnect of the high voltage supply of the x-ray diagnostics installation can be achieved in an embodiment wherein an integration unit is supplied with the output of the second read-out circuit, the integration unit in turn being connected to the high voltage supply through a threshold circuit. When the threshold is traversed, a disconnection of the high voltage supply occurs.

DESCRIPTION OF THE DRAWINGS

The invention shall be set forth in greater detail below with reference to the drawings.

FIG. 1 is a schematic illustration of a known x-ray diagnostics installation, of the type in which the principles of the present invention can be employed.

FIG. 2 is a block diagram of a video chain constructed in accordance with the principles of the present invention, suitable for use in an x-ray diagnostics installation of the type shown in FIG. 1.

DESCRIPTION OF THE PREFERRED EMBODIMENTS

FIG. 1 shows a convention x-ray diagnostics installation having an x-ray tube 1 which is driven by a high voltage generator 2 so as to emit a radiation beam which penetrates a patient 3, and casts a radiation image on the input luminescent screen of an x-ray image intensifier 4. The x-ray image intensifier 4 converts the radiation image into an optical image at the output luminescence screen. An optic system 5, which contains a base objective lens 6 and a camera objective lens 7, is coupled to the x-ray image intensifier 4. The output image of the x-ray image intensifier 4 is imaged by the lens 6 and 7 onto a video camera 8. The output signal of the video camera 8 is amplified in a video amplifier 9, and is reproduced on a monitor 10.

A partially reflecting mirror 11 is disposed in the parallel beam path of the optics system 5 and functions as a light distributor, which couples a portion of the light out of the parallel beam path between the lens 6 and 7. A further lens 12 produces an image on a light detector 13. The light detector 13 can be formed by a plurality of photo sensors arranged in a matrix. The output of the light detector 13 is connected to a measuring circuit 14, which includes a setting element 15 for selecting a specified value of the brightness of the light, and thus sets a corresponding level of the radiation dose. The measuring circuit 14 is connected to the high voltage generator 2, and de-energizes the x-ray tube 1 when the specified value is reached.

FIG. 2 shows a video camera 8 constructed in accordance with the principles of the present invention, which contains a semiconductor detector 16. The semiconductor 16 includes a plurality of pixels 17 arranged in a matrix, which serve to acquire the x-ray image pixel-by-pixel. The pixels 17 comprise a first group of pixels and are sampled by a first read-out circuit formed by shift registers 18 and 19. The output signals of these pixels 17 are supplied via the video amplifier 9 to an analog-to-digital converter 20. The digital output signal of the converter 20, as described below, is operated on in a processing circuit 21, is converted into an analog signal in a digital-to-analog converter 22, and is reproduced on the monitor 10.

Some of the pixels of the semiconductor 16, designated as a second group of pixels 23, are connected to a second read-out circuit composed of shift registers 24 and 25, which effect a read-out of the pixels 23. The read-out signals of the pixels 23 are supplied to an integration unit 26, which effects a summation of the signals from the selected pixels 23. The output signal of the integration unit 26 is supplied to a threshold circuit 27, wherein the signal is compared to a threshold, which can be set by an adjustment element 28. If and when this threshold is exceeded, the threshold circuit 27 supplies an output signal to the high voltage generator 2, causing the high voltage generator 2 to be shut off, and thereby de-energizing the x-ray tube 1.

The first read-out circuit formed by the shift registers 18 and 19 samples the pixels 17 of the first group at a first frequency, and supplies an output signal to the processing circuit 21. This output signal can be intermediately stored and further processed, such as by filtering, in the processing circuit 21. The processing circuit 21 also includes an interpolation circuit 29 which undertakes an interpolation between individual pixels 17 which are adjacent the pixels 23, so that the picture elements which are "lost", due to the lack of a signal at the location of the pixels 23 of the second group in the sampled signals of the first group, can be calculated and introduced into the output signals of the first group of pixels.

The first read-out circuit formed by the shift registers 18 and 19 operates at the frequency of the standard video clock. The second read-out circuit formed by the shift registers 24 and 25 operates at a second clock frequency which is higher than the standard video clock frequency. This permits the pixels 23, whose output signals are used for control of the x-ray diagnostics installation, to be multiply read-out during the normal cycle of the standard video clock, so that shorter switching times can be achieved. Since the standard video clock frequency is 50 Hz, the "normal cycle" has a duration of 20 ms. The precision of the term "off" point in time of the x-ray system is thereby enhanced.

The number and distribution of the pixels 23 comprising the second group can be selected by adjustment of the read-out circuit formed by the registers 24 and 25. All of the picture elements 23 shown in the drawing, individual ones of the picture elements 23, or a plurality of the pixels 23, which is less than the total number, can be selected for the exposure control, so that the dominant is freely selectable.

The construction and operation of an x-ray diagnostics installation in accordance with the principles of the present invention results in a simple structure since neither a light distributor for coupling out light corresponding to the image dominant, nor a light detector for the image dominant, are needed. As a result of the simple wiring of one semiconductor detector 16, a video signal is obtained using the standard frequency and time: constant while simultaneously permitting a test signal to be obtained for use in controlling the x-ray diagnostic installation, and this test signal is obtained at a higher frequency and thus at a substantially lower time constant. A fast control of the x-ray diagnostics installation is obtained as a result of driving the second group of pixels at a sampling frequency higher than the standard video frequency.

Although modifications and changes may be suggested by those skilled in the art, it is the intention of the inventors to embody within the patent awarded hereon all changes and modifications as reasonably and properly come within the scope of their contribution of the art.

We claim as our invention:

1. An x-ray diagnostics installation comprising:
   means for generating an x-ray image of a subject;
   an x-ray image intensifier having an input screen on which said x-ray image is incident, said x-ray image intensifier converting said x-ray image into an optical image at an output luminescent screen of said x-ray image intensifier;
   a semiconductor light detector disposed to detect said optical image on said output luminescent screen of said x-ray image intensifier, said semiconductor detector having a plurality of pixels arranged in a matrix at a surface of said semiconductor detector, said plurality of pixels including a plurality of pixels forming a first group and a separate plurality of pixels forming a second group, the plurality of pixels in said second group being small relative to the plurality of pixels in said first group, said pixels in said second group being arranged in a selected distribution over said surface of said semiconductor detector;
   first read-out circuit means for reading out said first group of pixels with a read-out clock at a first frequency to obtain a first read-out signal;
   means for generating a video image from said first read-out signal; second read-out circuit means for reading out said second group of pixels with a read-out clock at a second frequency which is higher than said first frequency, to obtain a second read-out signal; and
   means for controlling said means for generating an x-ray image dependent on said second read-out signal.

2. An x-ray diagnostics installation as claimed in claim 1, wherein said surface of said semiconductor detector has a central region, and wherein said pixels in said second group are arranged along the sides of a rectangle in said central region.

3. An x-ray diagnostics installation as claimed in claim 1, wherein said surface of said semiconductor detector has a central region, and wherein said pixels in said second group are arranged on a circle in said central region.

4. An x-ray diagnostics installation as claimed in claim 1, wherein each of said pixels of said semiconductor detector has an output signal associated therewith, and said x-ray diagnostics installation further comprising:

interpolation circuit means connected to said pixels in said first group for interpolating the output signals of pixels in said first group which are adjacent to pixels in said second group for generating an interpolated signal supplied to said first read-out circuit means as a substitute for a contribution to said video image which would be made by said pixels in said second group.

5. An x-ray diagnostics installation as claimed in claim 1, wherein said means for controlling said means for generating an x-ray image includes:

integration means connected to said second read-out circuit means, and supplied with said second read-out signal, for integrating said second read-out signal and generating an integrated signal; and threshold means, supplied with said integrated signal, for de-energizing said means for generating an x-ray image if said integrated signal traverses a threshold.

6. A method for operating an x-ray diagnostics installation comprising the steps of:

generating an x-ray image of a subject;

converting said x-ray image into an optical image;

detecting said optical image using a semiconductor detector having a plurality of pixels arranged in a matrix at a surface of said semiconductor detector;

dividing said plurality of pixels into a plurality a pixels forming a first group and a separate plurality of pixels forming a second group, the plurality of pixels in said second group being small relative to the plurality of pixels in said first group;

arranging said pixels in said second group in a selected distribution over said surface of said semiconductor detector;

reading out said first group of pixels with a read-out clock at a first frequency to obtain a first read-out signal;

generating a video image from said first read-out signal;

reading out said second group of pixels with a read-out clock at a second frequency which is higher than said first frequency, to obtain a second read-out signal; and controlling the generating of said x-ray image dependent on said second read-out signal.

7. A method as claimed in claim 6, wherein said surface of said semiconductor detector has a central region, and wherein the step of arranging said pixels in said second group in a selected distribution over said surface of said semiconductor detector is further defined by arranging said pixels in said second group along the sides of a rectangle in said central region.

8. A method as claimed in claim 6, wherein said surface of said semiconductor detector has a central region, and wherein the step of arranging said pixels in said second group in a selected distribution over said surface of said semiconductor detector is further defined by arranging said pixels in said second group on a circle in said central region.

9. A method as claimed in claim 6, wherein each of said pixels of said semiconductor detector has an output signal associated therewith, and comprising the further step of:

interpolating the output signals of pixels in said first group which are adjacent to pixels in said second group for generating an interpolated signal; and using said interpolated signal as a substitute for a contribution to said video image which would be made by said pixels in said second group.

10. A method as claimed in claim 6, wherein the step of generating an x-ray image includes the generation of x-ray radiation, and wherein the step of controlling the generation of said x-ray image includes the steps of:

integrating said second read-out signal and generating an integrated signal; and ceasing the generation of said x-ray radiation if said integrated signal traverses a threshold.

* * * * *